US00PP19357P2

(12) United States Plant Patent
Roberson

(10) Patent No.: US PP19,357 P2
(45) Date of Patent: Oct. 21, 2008

(54) ***LANTANA* PLANT NAMED 'ROBPWPUR'**

(50) Latin Name: *Lantana montevidensis*
Varietal Denomination: Robpwpur

(76) Inventor: Robert J. Roberson, 31706 E. Pink Hill Rd., Grain Valley, MO (US) 64029

( * ) Notice: Subject to any disclaimer, the term of this patent is extended or adjusted under 35 U.S.C. 154(b) by 0 days.

(21) Appl. No.: 11/978,115

(22) Filed: Oct. 25, 2007

(51) Int. Cl.
*A01H 5/00* (2006.01)

(52) U.S. Cl. ..... Plt./227

(58) Field of Classification Search ..... Plt./227
See application file for complete search history.

*Primary Examiner*—Annette H Para
(74) *Attorney, Agent, or Firm*—C. A. Whealy

(57) ABSTRACT

A new and distinct cultivar of *Lantana* plant named 'Robpwpur', characterized by its mounding and trailing plant habit; vigorous growth habit; relatively small leaves; freely flowering habit; and purple and white-colored flowers that are held above and beyond the foliage.

1 Drawing Sheet

Botanical designation: *Lantana montevidensis.*
Cultivar denomination: 'Robpwpur'.

BACKGROUND OF THE INVENTION

The present invention relates to a new and distinct cultivar of *Lantana,* botanically known as *Lantana montevidensis,* and hereinafter referred to by the name 'Robpwpur'.

The new *Lantana* is a product of a planned breeding program conducted by the Inventor in Grain Valley, Mo. The objective of the breeding program is to create new freely-flowering *Lantana* cultivars with attractive flower coloration.

The new *Lantana* is a naturally-occurring branch mutation of the *Lantana montevidensis* cultivar Alba, not patented. The new *Lantana* was discovered and selected by the Inventor on a single plant of the cultivar Alba in a controlled environment in Grain Valley, Mo. in July, 2002.

Asexual reproduction of the new *Lantana* by vegetative cuttings in a controlled environment in Grain Valley, Mo. since October, 2002, has shown that the unique features of this new *Lantana* are stable and reproduced true to type in successive generations.

SUMMARY OF THE INVENTION

The cultivar Robpwpur has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Robpwpur'. These characteristics in combination distinguish 'Robpwpur' as a new and distinct cultivar of *Lantana:*

1. Mounding and trailing plant habit.
2. Vigorous growth habit.
3. Relatively small leaves.
4. Freely flowering habit.
5. Purple and white-colored flowers that are held above and beyond the foliage.

Plants of the new *Lantana* can be compared to plants of the parent, the cultivar Alba. Plants of the new *Lantana* differ primarily from plants of the cultivar Alba in flower color as plants of the cultivar Alba have white-colored flowers. In addition, plants of the new *Lantana* have darker green-colored leaves than plants of the cultivar Alba.

Plants of the new *Lantana* can be compared to plants of the *Lantana* cultivar Weeping Lavender, not patented. Plants of the new *Lantana* differ from plants of the cultivar Weeping Lavender in the following characteristics:

1. Plants of the new *Lantana* have darker green-colored leaves than plants of the cultivar Weeping Lavender.
2. Plants of the new *Lantana* have darker purple-colored flowers than plants of the cultivar Weeping Lavender.

BRIEF DESCRIPTION OF THE PHOTOGRAPHS

The accompanying colored photographs illustrate the overall appearance of the new *Lantana,* showing the colors as true as it is reasonably possible to obtain in colored reproductions of this type. Colors in the photographs may differ slightly from the color values cited in the detailed botanical description which accurately describe the colors of the new *Lantana.*

The photograph at the bottom of the sheet comprises a side perspective view of a typical flowering plant of 'Robpwpur' grown in a container.

The photograph at the top of the sheet is a close-up view of typical inflorescences and leaves of 'Robpwpur'.

DETAILED BOTANICAL DESCRIPTION

The aforementioned photographs and following observations and measurements describe plants grown in Bonsall, Calif., under commercial practice during the spring and summer in an outdoor nursery with day temperatures ranging from 13° C. to 38° C. and night temperatures ranging from 10° C. to 24° C. Plants used in the photographs and for the description were grown in one-gallon containers for about four months. In the following description, color references are made to The Royal Horticultural Society Colour Chart, 1995 Edition, except where general terms of ordinary dictionary significance are used.

Botanical classification: *Lantana montevidensis* cultivar Robpwpur.

Parentage: Naturally-occurring branch mutation of *Lantana montevidensis* cultivar Alba, not patented.

Propagation:

*Type.*—By vegetative cuttings.

*Time to initiate roots, summer.*—About 12 to 14 days at 26° C.

*Time to initiate roots, winter.*—About 15 to 17 days at 20° C.

*Time to produce a rooted young plant, summer.*—About four weeks at 26° C.

*Time to produce a rooted young plant, winter.*—About five weeks at 20° C.

*Root description.*—Fibrous; thin; white in color.

*Rooting habit.*—Freely branching; moderately dense.

Plant description:

*Plant habit.*—Initially upright, then mounding and trailing plant habit. Freely branching habit; about four primary lateral branches per plant each with numerous secondary branches; pinching enhances lateral branch development; dense and bushy plant habit. Vigorous growth habit.

*Plant height.*—About 26 cm.

*Plant diameter.*—About 48 cm by 62 cm.

Lateral branch description:

*Length.*—About 34 cm.

*Diameter.*—About 3.5 mm.

*Internode length.*—About 1.7 cm to 2.2 cm.

*Strength.*—Strong.

*Texture, young.*—Pubescent; coarse.

*Texture, mature.*—Woody.

*Color, young.*—148A.

*Color, mature.*—199A to 199B.

Foliage description:

*Arrangement.*—Opposite, simple.

*Length.*—About 5.7 cm.

*Width.*—About 3.3 cm.

*Shape.*—Ovate.

*Apex.*—Acute.

*Base.*—Obtuse to attenuate.

*Margin.*—Serrate.

*Texture, upper and lower surfaces.*—Coarse, rough; minute pubescence.

*Venation pattern.*—Pinnate; arcuate.

*Color.*—Developing and fully expanded foliage, upper surface: 147A; venation, 147B. Developing and fully expanded foliage, lower surface: 147B; venation, 147C.

*Petiole.*—Length: About 8 mm. Diameter: About 1 mm. Texture, upper and lower surfaces: Pubescent. Color, upper surface: 146B. Color, lower surface: 147C.

Flower description:

*Flower arrangement and habit.*—Solitary tubular flowers arranged in hemispherical axially umbels; flowers face mostly upward or outward. Freely flowering habit with potentially two inflorescences developing per node, each umbel with about 28 flowers.

*Natural flowering season.*—Spring until frost in the autumn; flowering continuous during this period.

*Flower longevity on the plant.*—About four to five days. Flowers not persistent.

*Fragrance.*—Not detected.

*Inflorescence height.*—About 1.6 cm.

*Inflorescence diameter.*—About 3.6 cm.

*Flowers.*—Appearance: Flared trumpet, corolla fused, four-parted. Diameter: About 1 cm by 1.2 cm. Depth (height): About 1.9 cm.

*Flower buds.*—Length: About 1.2 cm. Diameter: About 4 mm. Shape: Elongate, oblong. Color: 75B.

*Corolla.*—Arrangement: Single whorl of four fused petals. Petal lobe length: About 3.5 mm to 5 mm. Petal lobe width: About 4 mm to 7 mm. Petal lobe shape: Roughly ovoid. Petal lobe apex: Rounded. Petal margin: Entire, slightly sinuate. Petal texture, upper surface: Smooth, glabrous. Petal texture, lower surface: Pubescent. Color: When opening, upper surface: 84B. When opening, lower surface: 84C. Fully opened, upper surface: 84A; towards the base, 155D; throat, 85B. Fully opened, lower surface: Towards the margins, 84A; center, 84C; towards the center, 155D; tube, 84A.

*Calyx.*—Appearance: Short and narrow tubular calyx. Length: About 2 mm. Diameter: About 1 mm. Sepal apex: Acute. Sepal margin: Entire. Sepal texture, upper surface: Smooth, glabrous. Sepal texture, lower surface: Pubescent. Sepal color, upper and lower surfaces: 145C.

*Peduncles.*—Length: About 4.8 cm. Diameter: Less than 1 mm. Strength: Strong. Texture: Pubescent. Color: 146B.

*Pedicels.*—Length: Less than 1 mm. Diameter: Less than 1 mm. Color: Close to 146B.

*Reproductive organs.*—Stamens: Quantity/arrangement: Four per flower, adnate to floral tube. Filament length: About 2 mm. Filament color: 155D. Anther shape: Oval. Anther length: Less than 1 mm. Anther color: 162A. Pollen amount: Scarce. Pollen color: 162A. Pistils: Quantity: One per flower. Pistil length: About 3 mm. Stigma shape: Rounded. Stigma color: 145A. Style length: About 1.5 mm. Style color: 145D. Ovary color: 145A. Fruits/seed: Fruit and seed development have not been observed.

Temperature tolerance: Plants of the new *Lantana* have been observed to tolerate temperatures from about 4° C. to about 38° C.

Pathogen/pest resistance: Plants of the new *Lantana* have not been observed to be resistant to pests and pathogens common to *Lantanas*.

It is claimed:

1. A new and distinct *Lantana* plant named 'Robpwpur' as illustrated and described.

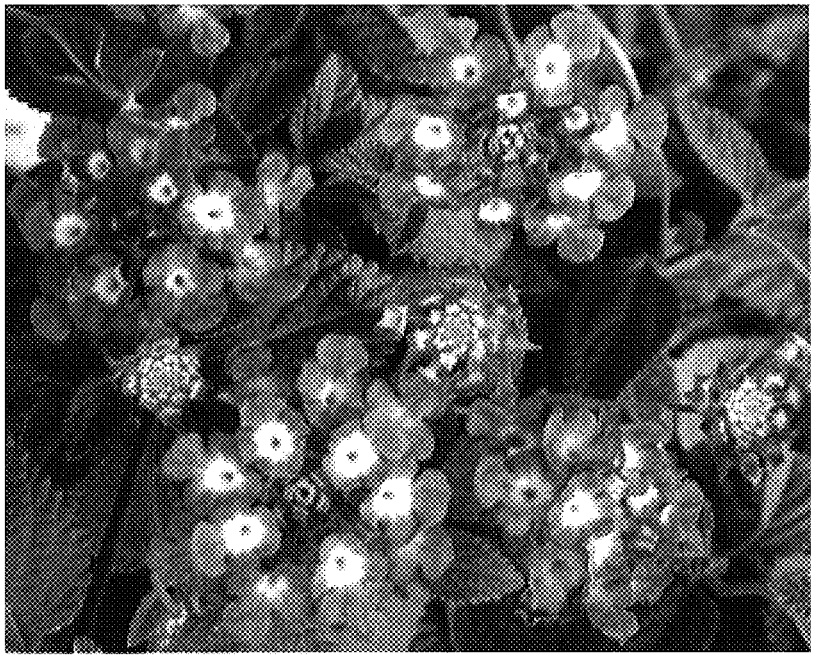
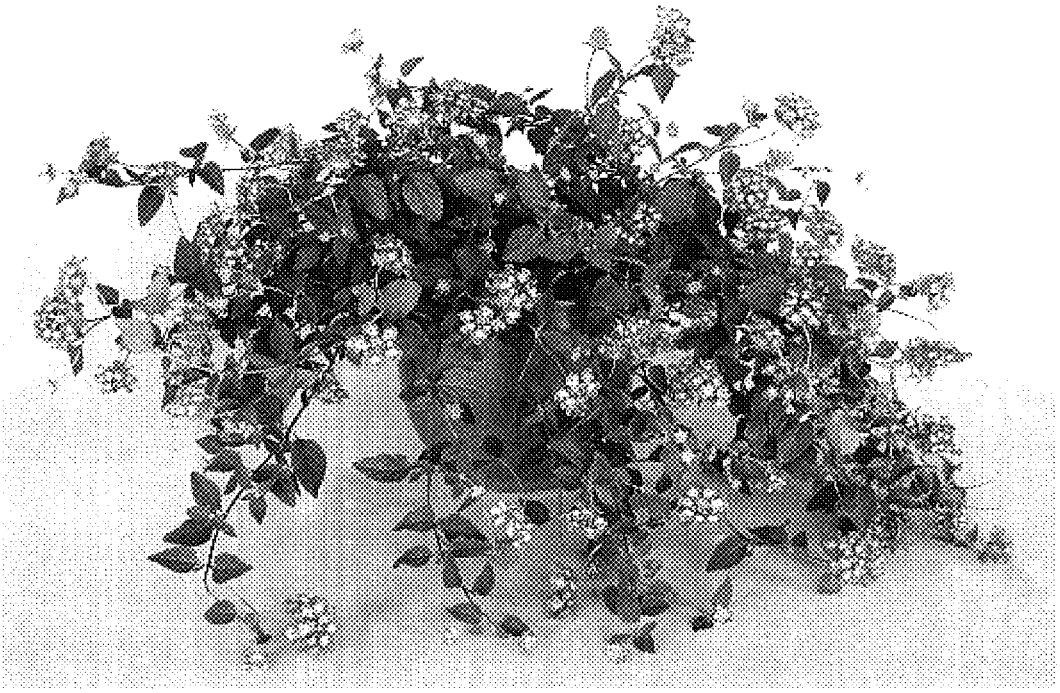

* * * * *